United States Patent [19]

Benninger

[11] 3,950,235
[45] Apr. 13, 1976

[54] ELECTROLYTIC METHOD OF PRODUCING BRANCHED PERFLUORO-ALKANES

[75] Inventor: Siegfried Benninger, Schwalbach, Taunus, Germany

[73] Assignee: Hoechst Aktiengesellschaft, Frankfurt am Main, Germany

[22] Filed: Nov. 15, 1974

[21] Appl. No.: 524,345

Related U.S. Application Data

[62] Division of Ser. No. 433,473, Jan. 15, 1974, abandoned.

[30] Foreign Application Priority Data

Jan. 17, 1973 Germany............................ 2302132

[52] U.S. Cl............................................... 204/59 F
[51] Int. Cl.²........................................... C25B 3/08
[58] Field of Search.................................... 204/59 F

[56] References Cited
UNITED STATES PATENTS
3,660,254   5/1972   Dunn................................. 204/59 F FOREIGN PATENTS OR APPLICATIONS
740,723   11/1955   United Kingdom............... 204/59 F Primary Examiner—R. L. Andrews
Attorney, Agent, or Firm—Curtis, Morris & Safford

[57] ABSTRACT

Branched perfluoro-olefins are electrofluorinated in an electrolytic cell at about 4–6.6 volts at a temperature of from 0° to 20°C together with anhydrous hydrogen fluoride. Branched perfluoro-alkanes are obtained in high yield.

6 Claims, No Drawings

ELECTROLYTIC METHOD OF PRODUCING BRANCHED PERFLUORO-ALKANES

This is a division of application Ser. No. 433,473 filed Jan. 15, 1974 now abandoned.

The present invention relates to branched perfluoro-alkanes.

As is generally known, perfluoro-alkanes are counted to a higher extent than fluorochlorohydrocarbons or perfluoroalkyl compounds among the chemically especially inert substances. Their chemical passivity to strong acids, lyes, oxidizing agents or reducing agents, such as for example alkali metals, with which they only react above the melting temperature thereof, has secured them a firm place in numerous fields of application (see, for example, R. D. Banks: "Fluorocarbons and their Derivatives", London 1964, page 115 et seq.; D. Osteroth: "Chemie und Technologie aliphatischer fluororganischer Verbindungen", Stuttgart, 1964). They are generally prepared by fluorination of corresponding aliphatic or aromatic hydrocarbons with elementary fluorine or certain transition metal fluorides, especially $CoF_3$; since, however, the last named metal fluorides are prepared and regenerated via $F_2$ also this process uses elementary fluorine. Apart from the great technological expenditure which is involved with the preparation, operation and reactions of the elementary fluorine, the above mentioned fluorination processes with $F_2$ have the great disadvantages that the product yields are often very poor: tar is formed and decomposition reactions occur with all the known results with regard to the economy of such a process. (M. Stacey, J. C. Tatlow, A. G. Sharpe, Advances in Fluorine Chem. Vol. 1, page 166 et seq. (1960) and Vol. 2, page 104 et seq. (1961)).

Attempts have, therefore, been made to obtain similar substances by avoiding the elementary fluorine. With this intention attempts were made repeatedly to use the Simons process for the electrochemical fluorination. The processes which have become known, however, offered no way out, since the electrofluorination of aromatic and olefinic hydrocarbons has proved impracticable on account of the quick anode blocking by the formation of polymer products on the anode surface; the electrofluorination of aliphatic hydrocarbons, on the other hand, is hindered decisively by their insolubility in hydrogen fluoride and generally gives only bad yields (M. Sander, W. Blochl, Chem. Ing. Techn. 37, 7 (1965)).

The fluorination of geminal difluoro-alkanes suggested by M. Sander and W. Blochl was an advancement over the state of the art at that time as far as the yields of perfluoro-alkanes are concerned (for example 32.8% for $C_{10}F_{18}$), however, this process involves expensive conversions of keto groups into the corresponding $CF_2$-groups in the preparation of the starting materials.

With the introduction of the perfluoroalkyl iodides the preparation of perfluor n-alkanes by the Wurtz synthesis became possible, but is must not be overlooked that also this method, too, is bound to $F_2$. The main disadvantage of this synthesis is, however, that it leads only to substantially unbranched perfluoroalkanes, which are characterized by considerably greater crystallization tendency, i.e. much higher solidification points, than strongly branched alkanes.

It was now found, most surprisingly, that the electrofluorination of branched perfluoro-olefins, contrary to the above mentioned negative experiences with unsaturated hydrocarbons, yields the corresponding perfluoroalkanes with excellent yields of partly above 80% of the theory.

The present invention provides a process for the preparation of branched perfluoro-alkanes by electrofluorination in an electrolytic cell with electrolyte circulation pump, wherein a branched perfluoro-olefin or a mixture of branched perfluoro-olefins together with anhydrous hydrogen fluoride is electrolyzed continuously or discontinuously at a temperature of between 0° and +20°C. It is important that the olefin to be fluorinated is added to the hydrogen fluoride without the addition of a conductive salt and, electrolyzed preferably at temperatures of between +4 and +10°C, with intensive electrolyte circulation in known manner, since on account of the unexpectedly good solubility conditions a sufficient current conductivity is provided through the dissolved perfluoro-olefin alone. The addition of a conductive salt proved very disadvantageous with regard to reduced product yields. These facts are in contrast to the experiences gained up to now according to which in the electrofluorination of olefins, aromatic compounds or alkanes, conductive salts were necessary (cf. for example, German Pat. Specification 1 040 009 or British Pat. Specification 758 492), is also as the functioning of the electrodes, unlimited in time, which are not blocked by any covering layer. The use of a circulating pump allows a good mixing of the system and a good supply to the electrode surface of fresh electrolyte. Thereby, better yields and higher current densities are possible than without a pump.

Not least, the product yields obtained on the average of over 70% of the theory - partly to almost 90% - present an important progress over processes of the state of the art. A special advantage of the branched perfluoroalkanes prepared according to the invention is that they are accessible without the technically expensive use of fluorine and that they can be produced, for example, from large-scale, starting products such as perfluoro-ethylene or propylene.

The process of the invention can be carried out discontinuously, but also continuously. In the latter case the circulated electrolyte is passed expediently over a separation vessel, so that with simultaneous continuous addition of dosed quantities of the olefin, part of the fluorinated product is drawn off and separated by fractionation from the unreacted starting product, which is led back again into the cell. This possibility is based on the fact that the alkanes of the invention boil on average at approximately 10°C higher than the perfluoro-alkenes used. Of course a continuous method of this type is limited to the fluorination of pure olefins with a sharp boiling point, since a mixture of different homologous olefins, as is obtained, for example, with the oligomerization of monomers such as tetrafluoroethylene or hexafluoropropene, must have a greater boiling range. If the electrofluorination of such a mixture is desired, it is carried out advantageously as a discontinuous process or, in the continuous method, the dosing speed and the current density are adjusted to one another in such a way that a higher, but not complete conversion is attained. Unreacted olefin must then be removed chemically, for example by oxidation with subsequent alkali washing, or by fractionation.

The particularly advantageous field of application of the invention is in the electrofluorination of branched perfluoro-olefins having a number of carbon atoms of from 6 to 12, without this indication limiting the application range. It is unimportant in which way these olefins are prepared. Preferably, the oligomers of tetrafluoroethylene or hexafluoropropene, which are easily accessible according to the present state of the art, are used. The oligomers $(C_2F_4)_n$ with $n = 2$ to 7 and $(C_3F_6)_m$ with $m = 2$ to 4 are especially suitable.

In the fluorination process also low fragments such as, for example, $C_2F_6$ and i-$C_8F_{18}$ from i-$C_9F_{18}$ are formed, although to a surprisingly low extent.

Olefin structures are cited below, which lead to the perfluorinated alkanes in the fluorination of the invention:

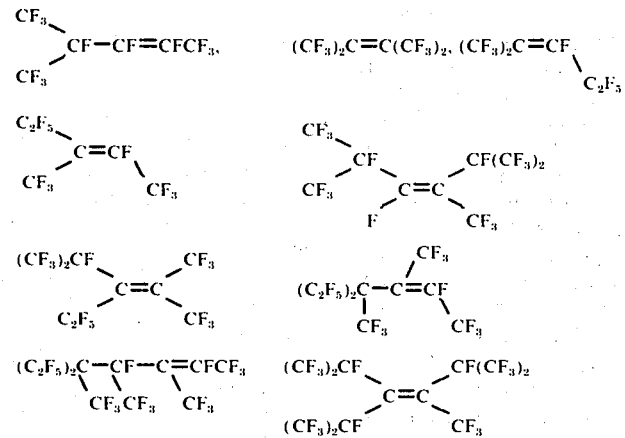

But also olefins with less than 6 carbon atoms can be fluorinated according to the process of the invention. Thus, for example, perfluoroisobutylene $(CF_3)_2C=CF_2$ yields the perfluorinated butane. The fluorination of gaseous olefins is carried out, expediently, at a slight excess pressure.

A further object of the invention is branched perfluoroalkanes with from 6 to 12 carbon atoms, containing no linear carbon chains with more than 3 carbon atoms, i.e. they are free from $(CF_2)_4$ or $(CF_2)_3CF_3$ groups.

Below, the formulae of some perfluoroalkanes of the invention are named which were characterized after distillative, or preparative gaschromatographic isolation by elementary analysis, mass spectra and NMR-spectra:

$(CF_3)_2CF(CF_2)_2CF_3$,  $(CF_3)_2CFCF(CF_3)_2$,
$(C_2F_5)_2CFCF_3$,
$(CF_3)_2CFCF_2CF(CF_3)CF(CF_3)_2$,
$C_2F_5CF(CF_3)CF(CF_3)C_2F_5$,
$(CF_3)_2CFCF(C_2F_5)CF(CF_3)_2$,
$(C_2F_5)_2C(CF_3)CF(CF_3)C_2F_5$,
$(C_2F_5)_2C(CF_3)CF(CF_3)CF(CF_3)C_2F_5$,
$((CF_3)_2CF)_3CC_2F_5$,
$(C_2F_5)_2CFCF(CF_3)_2$.

The perfluoro-alkanes accessible according to the invention are extremely valuable products. The addition of fluorine according to the invention means an important improvement for a number of uses. The substances within the scope of the invention present in many respects an advancement from the point of view of application as against the linear or cyclic perfluoroalkanes known up to now of the same number of carbon atoms since the generally high degree of ramification causes a considerable extension of the temperature range between boiling point, and solidification point or setting point. This means, for example, greater possibilities of application as inert, lubricating or cooling liquids at low temperatures. Contrary to the starting products, which possess these properites likewise to a large extent and are also used in the way mentioned, the products of the invention have the decisive advantage of being chemically considerably more inert; the starting products can, for example, be oxidized by permanganate solution. Also, due to the smaller dielectric constants, the alkanes have better utilitarian properties as dielectrics. The lower homologs are also of interest as propellants for turbines.

Since it is not important for the functioning of the fluorination process according to the invention whether a mixture of olefins of various molecular sizes or a chemically and physically uniform olefin is used, the choice of the starting products as regards their molecular size can be adapted exactly to the intended application. This is valid for the extent of the boiling range as well as for the height thereof of the perfluoroalkanes required. In other words, the invention offers the possibility of preparing a perfluoroalkane mixture with a large boiling range by fluorination of a corresponding perfluoro-alkene mixture, but also, by using homogeneous olefins, of obtaining homogeneous perfluoroalkanes; homogeneous refers in this connection also to isomer mixtures with the same number of carbon atoms but of varying position of the double bond in the framework, as well as to structural isomers with different ramifications.

In the following examples the electrofluorination was carried out in a so-called Simons cell of the usual construction. It consisted of a vessel of stainless steel of approximately 1.5 liters content, which was provided with a cooling jacket and a bundle of parallel nickel plates as electrodes. The anode surface was 30.8 $dm^2$, the plate distance was 2.5 mm. The cell was further provided with a reflux condenser cooled at $-78°C$, a liquid level indicator as well as a circulation pump and a device for waste gas washing. The current density was kept at between 0.2 and 1.6 $A/dm^2$, generally, however, between 0.5 and 1.0 $A/dm^2$. The electrolysis voltage was kept at between 4.0 and approximately 6.6 V, the temperature between +4 and +10°C.

The perfluoro-alkanes withdrawn from the cell were freed from hydrogen fluoride with aqueous alkali lye or solid sodium fluoride and tested IR-spectroscopically for the presence of the olefinic double bonds. With a positive test (absorptions at 5.8 or 6.1 $\mu$), the product was after-fluorinated in the cell. The gaschromatographic product analysis, carried out with a porasil- or silicone ribber column, served for the quantitative determination of unreacted olefin portions as well as for the characterization and determination of the perfluoro-alkanes formed. Small olefinic remains possibly still present were destroyed before the fractionation of the product by an acetonic solution of $KMnO_4$.

Also unbranched and cyclic perfluoro-alkanes can be obtained by electrofluorination, which is, however, only of minor interest on account of the difficult accessibility of the corresponding perfluoro-alkenes.

The current yields ascertained in the following examples are contrary to the substance yields, not typical of the process, because of the short running time of the fluorination process, since only the current passed after a relatively long inhibitory time at the beginning of the experiment is of importance for the current yield.

The following examples illustrate the invention.

EXAMPLE 1:

1350 of anhydrous hydrogen fluoride and 150 g of perfluoro-hexene of the formula $(CF_3)_2C=CF(C_2F_5)$ were introduced into the laboratory cell described above. In the course of 22 hours, 357 g of $C_6F_{12}$ were added in several portions. The product, insoluble in hydrogen fluoride, and always drawn off before a further addition of olefin, was found to be free from starting products, in each case determined IR-spectroscopically and gaschromatographically. With a current density of on an average 0.6 A/dm$^2$, at an electrolysis temperature of +5°C and a voltage range of from 4.9 to 6.1 V a yield of 411 g of the alkane $C_6F_{14}$, corresponding to approximately 78 per cent of the theory, was found. The product withdrawn from the cell was, according to the IR-spectrum and gas-chromatogram, completely free from perfluoro-olefins. After removing the hydrogen fluoride by alkaline washing, a uniform boiling point of 57.7°C/760 mm Hg was found by fractionation; the boiling point of the starting product was from 46 to 47°C. The structure was $(CF_3)_2CF(CF_2)_2CF_3$ according to the mass and NMR-spectrum (highest mass peak at $m/e = 319$, corresponding to M-F).

Analysis: found: 21.2 % C; 78.3% F; calculated: 21.3% C; 78.7% F.

EXAMPLE 2:

In the same electrolytic cell in the course of 28 hours 480 g of a perfluorononene mixture were fluorinated, which mixture consisted to 63% by area of $(CF_3)_2C=C(C_2F_5)CF(CF_3)_2$ and to 34% by area of the isomer $((CF_3)_2CF)_2 C = CF(CF_3)$ according to gas-chromatographic analysis. The process, carried out at an electrolysis temperature of +5°C, a voltage of 4.4 to 6.1 V and a mean current density of 0.85 A/dm$^2$, yielded 392 g, corresponding to 75% of the theory, of a perfluorononene product, which, according to the IR-spectrum, no longer contained any double bond bands. The gas-chromatogram showed 4 new components. The determination of the structure gave the following result:

1. $(CF_3)_2CFCF(C_2F_5)_2$ :
   62.3% by area; highest mass peak at
   $m/e = 369$, corresponding to M-F.

Analysis: Found: 21.0% C; 77.2% F calculated: 21.9% C; 78.1% F

2. $((CF_3)_2CF)_2CFC_2F_5$ :
   29% by area; highest mass peak at
   $m/e = 469$, corresponding to M-F.
   Analysis: found: 21.7% C; 78.1% F calculated: 22.1% C; 77.8% F.

The structures of the substances named under 1) and 2) were ascertained by the NMR-spectra.

For a secondary component of 4% by area, the structure $((CF_3)_2CF)_2CFCF_3$ is probable on account of the mass spectrum. A further secondary component of small concentration was not analysed more closely. The fractionation yielded 2 fractions with the boiling points of 102 to 104°C/760 mm Hg (component 1) and 120 to 121°C/760 mm HG (component 2).

EXAMPLE 3:

475 g of the isomer mixture of branched perfluoro-alkenes fluorinated in Example 2 were subjected to electrolysis in an analogous way at a working temperature of +10°C. The product, fluorinated for 15 hours at a voltage of 4.3 to 5.6 V and a current density of 0.7 A/dm$^2$, showed in the gas-chromatographic analysis the substances mentioned in Example 2 and also a total of 20% by area of the starting olefins. The product, obtained in a yield of 305 g, was separated by fractionation into the alkanes with the boiling ranges given in Example 2 and the olefinic components with the boiling range 110 to 116°C. The yield of alkanes was 48% of the theory.

EXAMPLE 4:

Perfluoro-3,4-dimethyl-hexane boiling at 102° to 104.5°C was obtained in a good yield in the apparatus described in Example 1 by electrofluorination of perfluoro-3,4-dimethylhexene-(2).

EXAMPLE 5:

Analogously to Example 4, perfluoro-3-methylpentane (boiling point 56° to 57.5°C) was obtained by electrofluorination of perfluoro-3-methylpentene-(2).

What is claimed is:

1. A method for making a branched perfluoroalkane by electrofluorination in an electrolytic cell, which method comprises continuously or discontinuously electrolyzing an electrolyte, consisting essentially of anhydrous hydrogen fluoride and of at least one branched perfluoro-olefin having 6 to 12 carbon atoms, at a temperature from 0° to 20°C. and at a voltage from 4 to about 6.6 volts.

2. A method as in claim 1 wherein said perfluoro-olefin has from 6 to 9 carbon atoms.

3. A method as in claim 1 wherein said perfluoro-olefin is an oligomer of tetrafluoroethylene or of hexafluoropropene.

4. A method as in claim 1 wherein said perfluoro-olefin is a mixture of structural isomers having the same number of carbon atoms.

5. A method as in claim 1 wherein the electrolyte is electrolyzed at a temperature from 4°C. to 10°C.

6. A method as in claim 1 wherein the electrolyte is circulated in said electrolytic cell by a circulation pump.

* * * * *